United States Patent
Wärnberg

(10) Patent No.: US 7,016,454 B2
(45) Date of Patent: Mar. 21, 2006

(54) DEVICE FOR DISPLAYING X-RAY IMAGES OF AN OBJECT

(75) Inventor: Bo Wärnberg, Linköping (SE)

(73) Assignee: Swemac Medical Appliances AB, Linkoping (SE)

( * ) Notice: Subject to any disclaimer, the term of this patent is extended or adjusted under 35 U.S.C. 154(b) by 0 days.

(21) Appl. No.: 10/508,040

(22) PCT Filed: Mar. 17, 2003

(86) PCT No.: PCT/SE03/00436

§ 371 (c)(1),
(2), (4) Date: Sep. 16, 2004

(87) PCT Pub. No.: WO03/077762

PCT Pub. Date: Sep. 25, 2003

(65) Prior Publication Data

US 2005/0116878 A1    Jun. 2, 2005

(30) Foreign Application Priority Data

Mar. 19, 2002    (SE) .................................... 0200813

(51) Int. Cl.
*H05G 1/70*    (2006.01)
*H05G 1/02*    (2006.01)
(52) U.S. Cl. .......................................... 378/9; 387/197
(58) Field of Classification Search .................... 378/9, 378/17, 92, 98, 98.5, 41, 42, 197, 101
See application file for complete search history.

(56) References Cited

U.S. PATENT DOCUMENTS 4,435,830 A * 3/1984 Suzuki et al. ................ 378/197

(Continued)

FOREIGN PATENT DOCUMENTS

DE    42 24 614 A1    1/1994

(Continued)

Primary Examiner—Edward J. Glick
Assistant Examiner—Irakli Kiknadze
(74) Attorney, Agent, or Firm—Tarolli, Sundheim, Covell & Tummino LLP.

(57) ABSTRACT

The present invention relates to a device for displaying X-ray images of an object, preferably in connection with surgical orthopaedic operations, wherein X-ray images of the object are generated by means of at least a first and a second X-ray device (19, 20). The first X-ray device (1)=is provided to X-ray the object in a first plane (P1) and the X-ray images obtained thereby are displaced on a first screen (28) and the second X-ray device (20) is provided to X-ray the object in a second plane (P2) and the X-ray images obtained thereby are displayed on a second screen (30). An automatic image changing device (AC) includes an image alternator (54) which is provided to automatically change the display of moving images of the object taken in one plane (P1) on the first screen (28) to display of moving images of the object taken in the other plane (P2) on the second screen (30) and vice versa, such that it becomes possible to see moving X-ray images of the object taken in the two different planes (P1 and P2) close behind each other. Each receiver (22 and 24 respectively) in each X-ray device (19 and 20 respectively) is linearly displaceable relative to the associated transmitter (21 and 23 respectively) and/or each transmitter (21 and 23 respectively) is linearly displaceable relative to each receiver (22 and 24 respectively) for varying the distance between each receiver (22 and 24 respectively) and transmitter (21 and 23 respectively).

11 Claims, 3 Drawing Sheets

U.S. PATENT DOCUMENTS

| | | |
|---|---|---|
| 5,515,416 A | 5/1996 | Siczek et al. |
| 5,546,440 A | 8/1996 | Nakatani et al. |
| 5,835,557 A | 11/1998 | Malmstrom |
| 5,923,721 A * | 7/1999 | Duschka .................... 378/92 |
| 5,967,982 A | 10/1999 | Barnett |
| 6,104,780 A * | 8/2000 | Hanover et al. .............. 378/92 |
| 6,431,751 B1 * | 8/2002 | Everett et al. .............. 378/197 |

FOREIGN PATENT DOCUMENTS

EP        0 917 856 A1    5/1999

* cited by examiner

DEVICE FOR DISPLAYING X-RAY IMAGES OF AN OBJECT

The present invention relates to a device for displaying X-ray images of an object, preferably in connection with surgical orthopaedic operations, wherein X-ray images of the object are generated by means of at least a first and a second X-ray device. The first X-ray device is provided to X-ray the object in a first plane and the X-ray images obtained thereby are displayed on a first screen and the second X-ray device is provided to X-ray the object in a second plane and the X-ray images obtained thereby are displayed on a second screen. The first X-ray device comprises a transmitter and a receiver and the second X-ray device comprises a transmitter and a receiver. The X-ray devices are provided on one and the same arm, which is shaped as a part or segment of a circle and located on a mobile unit. A first screen is provided for displaying X-ray images from the first X-ray device and a second screen is provided for displaying X-ray images from the second X-ray device. A unit separate from the mobile unit includes the first as well as the second screen.

The publication U.S. Pat. No. 5,835,557 relates to a mobile X-ray plant with two X-ray devices for taking an X-ray of an object in two planes, e.g. in connection with surgical orthopaedic operations. At this X-ray plant, the change or succession of images is controlled manually, which means a slow and thus, in many cases disadvantageous change or succession of images.

The publication EP 0 917 856 refers to a device and method for X-ray reproduction with two X-ray devices showing or reproducing an object in two different planes. The reproduction in the first plane is displayed on a first screen and the reproduction in the second plane is displayed on a second screen. When the system is started, the first reproduction system takes a picture which is displayed on the first screen. The second system is automatically triggered to start and both systems produce a sequence of pictures or images which are displayed continuously on the respective screen, but both screens are not brought to display moving pictures or images.

The object of the present invention has been to provide a device for automatic change or succession of moving pictures or images between two screens, to easily be able to read the moving X-ray images at the successions of images and to be able to adapt the X-ray accuracy to different objects to be X-rayed. This is arrived at by providing the device defined above with the characterizing features of primarily subsequent claim 1.

Since the device when displaying X-ray images includes an image alternator which automatically alternates between or changes from moving X-ray images taken in one plane and displayed on a first screen to moving X-ray images taken in another plane and displayed on a second screen, the momentaneous position of the object being X-rayed can be determined precisely. Since both screens are provided on one and the same frame, it is easy to read the X-ray images during the change and since the receivers in the X-ray device are movable relative to the transmitters, the X-ray accuracy can be adapted to different objects to be X-rayed.

The invention will be further described below with reference to the accompanying drawings, in which FIG. 1 is a perspective view of a device according to the invention;

Figure 1:
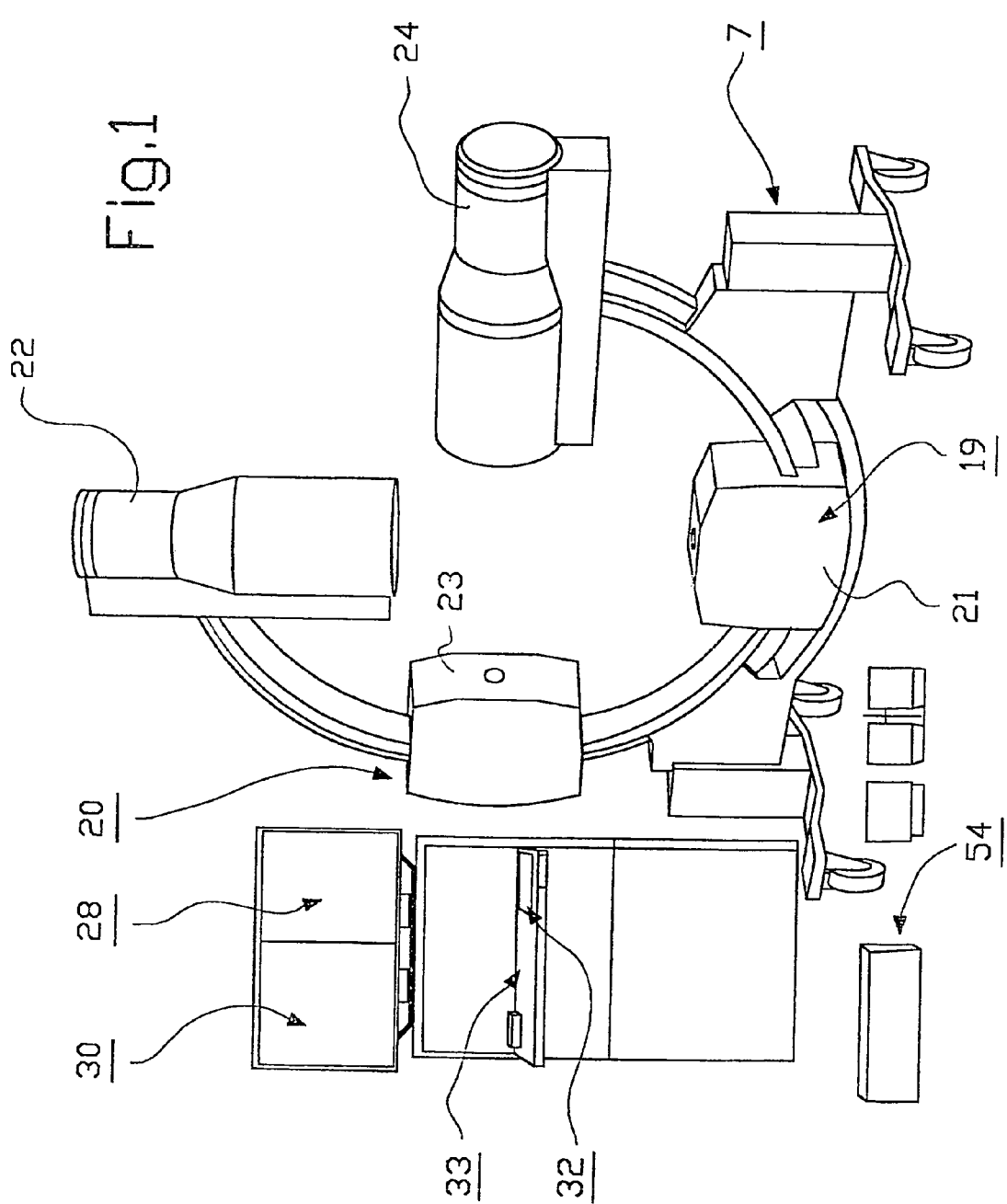
Figure 2:
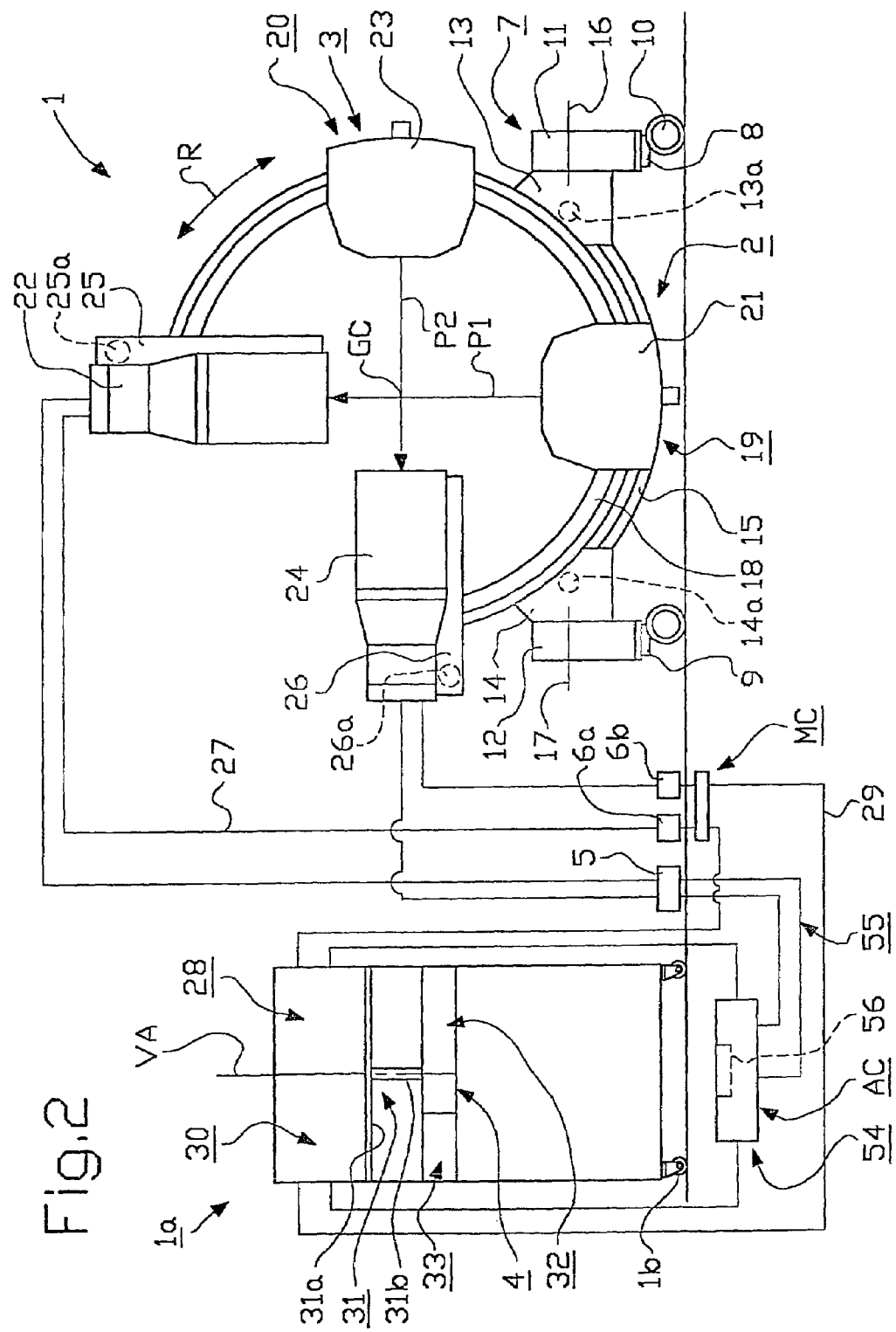
FIG. 2 is a side view of the device of FIG. 1.

The device illustrated in the drawings is adapted for use in connection with surgical orthopaedic operations and comprises a mobile unit 1 with two X-ray systems 2, 3. There is also a control centre 4, a device AC for automatic change or succession of images and including a foot pedal 5 and eventually a device MC for manual change or succession of images which may include two foot pedals 6a, 6b.

The mobile unit 1 includes a chassis frame 7 with two wheel units 8, 9, each of which comprising two wheels 10 and a vertical column 11, 12. Each column 11 and 12 respectively, has two parts, namely a first part which is attached to the respective wheel unit 8, 9 and a second part which is telescopically adjustable relative to the first part by means of lifting devices (not shown). Arm brackets 13 and 14 respectively, are provided on the vertically adjustable second parts of the columns 11 and 12 respectively, and these arm brackets 13 and 14 respectively, may be rotatable about a horizontal or substantially horizontal axis 16 and 17 respectively, relative to other parts of the columns 11, 12. The arm brackets 13 and 14 respectively, are interconnected through a connecting member 15.

An arcuate arm 18, shaped preferably as a part or segment of a circle or substantially as a part or segment of a circle, and with a geometrical centre in a point GC, is open at a location at the top. This arm 18 is movably mounted on the arm brackets 13, 14 such that it can be pivoted in opposite directions R about said geometrical point GC. This rotation or pivoting movement of the arm 18 can be accomplished by means of one or more turning devices 13a and/or 14a.

A first X-ray device 19 in the first X-ray system 2 is provided on the arm 18 and so is also a second X-ray device 20 in the second X-ray system 3.

The first X-ray device 19 is adapted to X-ray an object (not shown) in a first plane P1 and the second X-ray device 20 to X-ray the object in a second plane P2, which preferably is perpendicular to the first plane P1. The first X-ray device 19 includes a first transmitter 21 (an X-ray tube or X-tube) for emitting X-rays and a first receiver 22 (e.g. image intensifier or semiconductor sensors) for receiving X-rays emitted by the first transmitter 21 and having passed through said object. The first transmitter 21 may be located down below on the arm 18 and the first receiver 22 at the top of the arm 18.

The second X-ray device 20 includes a second transmitter 23 (X-ray tube or X-tube) for emitting X-rays and a second receiver 24 (image intensifier) for receiving X-rays emitted by the second transmitter 23 and having passed through said object. The second transmitter 23 and the second receiver 24 may be located on the arm 18 in the middle between the first transmitter 21 and the first receiver 22.

The transmitter 21 and receiver 22 of the first X-ray device 19 and the transmitter 23 and receiver 24 of the second X-ray device 20 are preferably mounted on the arm 18 non-rotatable relative to each other about the point GC.

The arm 18 defines together with the transmitters 21, 23 and receivers 22, 24 of the X-ray devices 19, 20 a substantially G-shaped device.

The first and second X-ray devices 19, 20 are preferably provided relative to each other such that the X-rays emitted by the transmitters 21 and 23 in the planes P1 and P2 and received by the receivers 22, 24, intersect each other in the point GC.

For being able to vary the distance between the first transmitter 21 and the first receiver 22, the first receiver 22 can be movably mounted on the arm 18 through a first bracket 25 which permits linear displacement of said receiver 22 relative to the first transmitter 21. For being able to vary the distance between the second transmitter 23 and the second receiver 24, the second receiver 24 can be movably mounted on the arm 18 through a second bracket 26 which permits linear displacement of said receiver 24 relative to the second transmitter 23. Movement or displacement of the receivers 22, 24 may occur by means of operating devices 25*a*, 26*a* which preferably are provided on the brackets 25, 26 and which eventually are remote radio controlled.

Alternatively, the transmitters 21, 23 may be displaced linearly relative to the receivers 22, 24 or may receivers 22, 24 and transmitters 21, 23 be linearly movable relative to each other.

The units 22, 24 and/or 21, 23 are linearly movable in parallel with the planes P1, P2 in which the X-rays are directed from the respective transmitter 21, 23 to the respective receiver 22, 24.

The X-ray images obtained in the first receiver 22 are transmitted through a first line 27 to a first screen 28 (so called TV-monitor) to be displayed thereon and the X-ray images obtained in the second receiver 24 are transmitted through a second line 29 to a second screen 30 (so called TV-monitor) for display thereon. The transmission of the images from the receivers 22, 24 may alternatively occur Tirelessly. In the line 27 there is the foot pedal 6*a* for activating the display of the images on the first screen 28 and in the line 29 there is the foot pedal 6*b* for activating the display of X-ray images on the second screen 30.

The screens 28, 30 are preferably provided on a separate unit 1*a* separated from the mobile unit 1. This separate unit 1*a* can be mobile by means of driving wheels 1*b*. The screens 28, 30 can be located on a frame 31 comprising a carrier member 31*a* on which the screens 28, 30 are mounted and a pivoting member 31*b*, e.g. a column, through which the carrier member 31*a* is provided on the separate unit 31*a* such that said carrier member 31*a* and thereby, the screens 28, 30 are pivotable or rotatable about a vertical geometric axis VA.

The control centre 4 preferably forms part of the separate unit 1*a* and may comprise a manually operable control means for controlling or operating the X-ray device.

The control centre 4 may further comprise a display panel 32 and the control means may be a number of manually operable controls, such a e.g. main circuit-breaker, controls for X-ray data settings, controls for setting of radioscopy, controls for operating motor-driven diaphragms, controls for setting of magnification, controls for TV-light setting and so on. The control centre 4 may also comprise a control screen 33 showing the result of the settings and it is preferably located beneath the screens 28, 30.

The advantage by providing the screens 28, 30 and the control centre 4 on one and same separate unit 1*a* is that personnel does not need to move within the sterile area in order to operate the controls nor need to stand such that they stand in the way of the screens 28, 30 for other persons.

Figure 3:
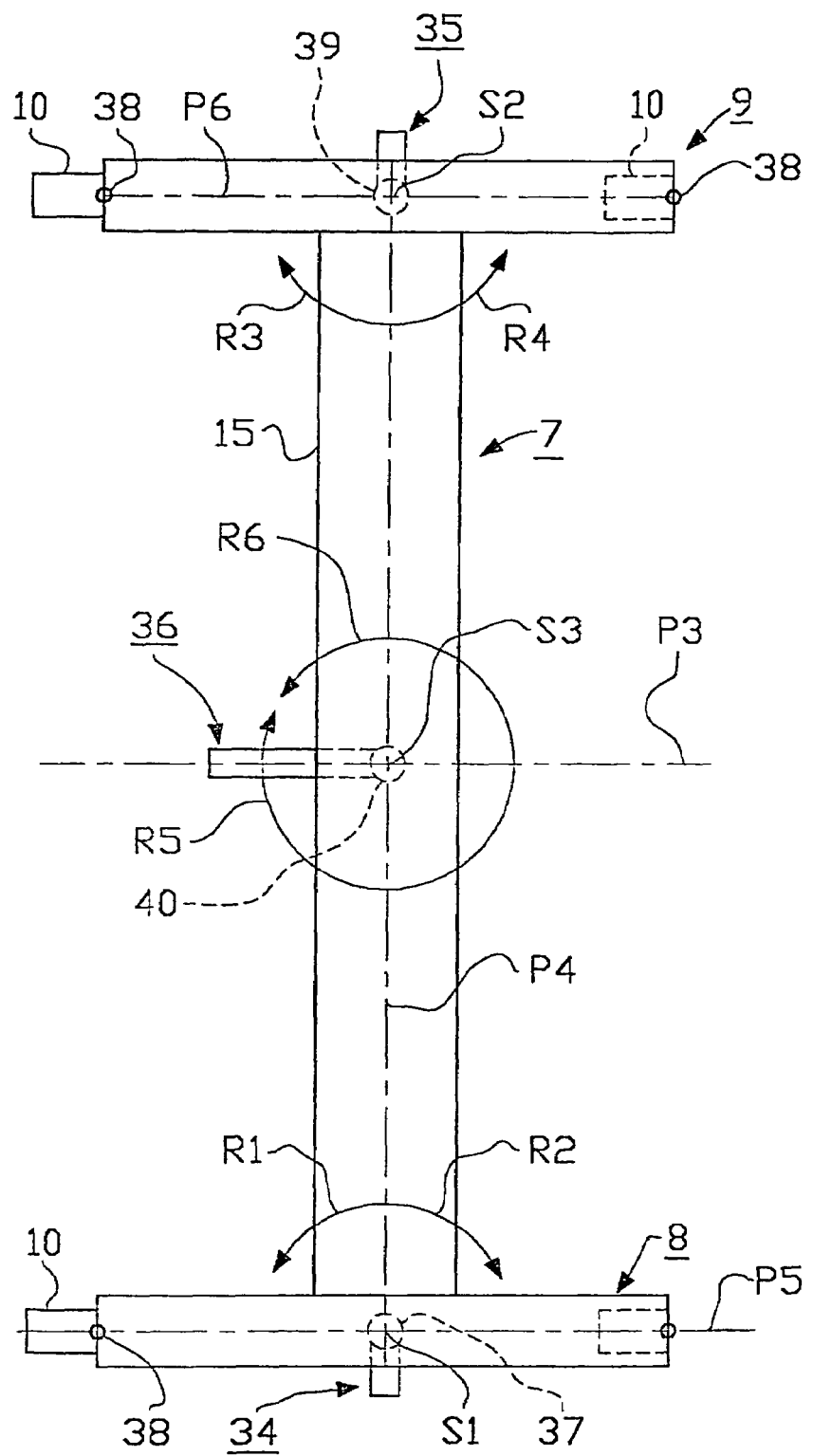
FIG. 3 are schematic plan views of the device of FIGS. 1 and 2 and about which points the device is movable after braking thereof.

The chassis frame 7 may comprise a first brake device 34 and/or a second brake device 35 and/or a third brake device 36. The first brake device 34 is provided on the wheel unit 8 and may include a first brake means 37 in the form of a brake shoe or similar which can be brought to engage the floor with great friction in a first point of intersection S1 between a fourth vertical plane P4 (see FIG. 3) midway between or substantially midway between the wheels 10 of the wheel unit 8 and a fifth vertical plane P5, in which vertical axes of rotation 38 are found, about which the wheels 10 of the wheel unit 8 are pivotable relative to the chassis frame 7. The plane P4 is also a vertical plane in which the point GC where the planes P1 and P2 intersect each other, is found. By means of said first brake device 34, the chassis frame 7 can be swung or turned in opposite directions R1 and R2 about the first brake means 37, i.e. about the point of intersection S1 when said brake means 37 is in its active position. When required, the chassis frame 7 can be swung back or returned to an initial position.

The second brake device 35 is provided on the wheel unit 9 and may include a second brake means 39 which can be brought to engage the floor in a second point of intersection S2 between the fourth vertical plane P4 and a sixth vertical plane P6 in which vertical axes of rotation 38 are found, about which the wheels 10 of the wheel unit 9 are pivotable relative to the chassis frame 7. This second brake device 35 permits swinging or turning of the chassis frame in opposite directions (R3 and R4) about the point of intersection S2 and back to an initial position.

The third brake device 36 may comprise a third brake means 40 which can be brought to engage the floor in a third point of intersection S3 between the third and fourth vertical plane P3, P4. The third brake device 36 permits swinging or turning of the chassis frame 7 in directions R5 and R6 about the point of intersection S3 midway between or substantially midway between the wheel units 8, 9 and back to the initial position. The chassis frame 7 can be swung 360° about the point of intersection S3. The planes P5 and P6 are parallel and these planes as well as the plane P3 intersect the plane P4 perpendicularly.

As is shown in the drawings, the wheels 10 are preferably castor wheels which may be locked in different positions for various purposes. Castor wheels and locking devices therefor are however commonly known in similar connections and are therefor not further described here.

Before starting operation of the device described above, the proper settings are carried through regarding said operating conditions as well as the position of the device relative to the object to be X-rayed. Therefore, the display of the X-ray images is accomplished by activating the foot pedals 6*a*, 6*b* or corresponding members. Thus, by activating the food pedal 6*a*, display of moving X-ray images taken by the first X-ray device 19 in plane P1 is made on the first screen 28. For changing the display of X-ray images, the foot pedal 6*a* is deactivated and instead, the foot pedal 6*b* is activated. When the foot pedal 6*a* is deactivated, the X-ray image on the first screen 28 is frozen, and when the foot pedal 6*b* is activated, display of moving X-ray images taken by the second X-ray device 20 in the plane P2 is instead made on the second screen 30. This manual change or succession is repeated the required number of times during operation.

The device AC for automatic change of the display of images between the two screens 28, 30 without interruption or at least without substantial interruption may comprise an image alternator 54 which automatically alternates between or changes the display of images from the first screen 28 to the second screen 30 and vice versa. Hereby, it is possible to see moving X-ray images of the object taken in the two different planes P1 and P2 close behind each other, which substantially improves the perspicuity of the object during operation in the two planes P1 and P2.

The image alternator 54 may be located in a line circuit 55 connecting the receivers 22 and 24 respectively, of the X-ray devices 19, 20 with the respective screen 28, 30. In this line circuit 55, the foot pedal 5 (or a similar manually operable control device) may also be connected and the image alternator 54 can be controlled such that the change or succession of images occurs during a display procedure, the duration of which is determined by the time the foot pedal 5 is activated.

The image alternator 54 may e.g. carry through image changes within an interval from two image changes per second to one image change per two seconds. In a first part of each display of an image, moving X-ray images can be displayed and these images can then be frozen to be immovable during a second part of said display. The moving images may e.g. be displayed about 25 X-ray images/second.

The immovable X-ray images may e.g. be maintained on one of the screens 28, 30 when automatic change or succession is carried through for displaying moving X-ray images on the other of said screens 28, 30, and the immovable X-ray images can be maintained on one of the screens 28, 30 at least while moving X-ray images are displayed on the other of said screens 28, 30.

The foot pedal 5 can be activated such that a display interval may include only one automatic change of image from one screen 28, 30 to the other. An image display however, may also include several automatic changes of images between the screens 28, 30. In said latter case, an automatic change of image from one of the screens 28, 30 to the other occurs, followed by an automatic change of image from one of the screens 30, 28 to the other and so on until the desired number of automatic changes of images have been carried through.

The invention is not limited to the device described above, but may vary within the scope of the subsequent claims. It should be mentioned that the X-ray device may comprise a character generating device 56 generating characters, e.g. lines, on the screens 28, 30, said characters being adapted to help the surgeon or corresponding doctor to locate the operating instruments in correct positions relative to the object to be operated. It should also be mentioned that said X-ray device is not limited for use in connection with surgical orthopaedic operations, but can be used within entirely different technical fields.

What is claimed is:

1. Device for displaying X-ray images of an object, preferably in connection with surgical orthopaedic operations, said device comprising:

at least a first X-ray device (19) and a second X-ray device (20) for generating X-ray images of the object, said first X-ray device (19) being configured to X-ray the object in a first plane (P1) and obtain the X-ray images of the object, said second X-ray device (20) being configured to X-ray the object in a second plane (P2) and obtain the X-ray images of the object;

a first screen (28) operatively associated with said first X-ray device (19), said first screen (28) being responsive to said first X-ray device (19) to display the X-ray images obtained by said first X-ray device (19);

a second screen (30) being operatively associated with said second X-ray device (20), said second screen (30) being responsive to said second X-ray device (20) to display the X-ray images obtained by said second X-ray device (20), wherein said first X-ray device (19) comprises a transmitter (21) and a receiver (22), said receiver of said first X-ray device being linearly displaceable relative to said transmitter (21) of said first X-ray device (19) for varying the distance between said transmitter (21) of said first X-ray device (19) and said receiver (22) of said first X-ray device (19), said second X-ray device (20) comprising a transmitter (23) and a receiver (24), said receiver of said second X-ray device (20) being linearly displaceable relative to said transmitter (23) of said second X-ray device (20) for varying the distance between said transmitter (23) of said second X ray device (20) and said receiver (24) of said second X-ray device (20);

a mobile unit (1) including a chassis frame (7), said chassis frame (7) including two wheel units (8, 9) each with one column (11, 12), each column (11 and 12 respectively) includes a first and a second part, of which the second part is telescopically vertically adjustable relative to the first part, said chassis frame comprising at least one brake device (34 and/or 35 and/or 36), said brake device (34 and/or 35 and/or 36) including at least one brake apparatus (37 and/or 39 and/or 40) which can be brought to engage, in an active position or active positions, a floor in a point (S1 and/or S2 and/or S3) such that the chassis frame (7) can swing or pivot about said point (S1 and/or S2 and/or S3);

an arm (18), which is shaped as a part or a segment of a circle, provided on said chassis frame (7), said first and second X-ray devices (19, 20) being provided on said arm (18);

an arm bracket (13 and 14 respectively) for the arm (18) being provided on the second part of each column (11 and 12 respectively) and pivotable about a horizontal geometric axis (16 and 17 respectively);

a connecting member (15) that interconnects the arm brackets (13, 14);

a control center (4) for controlling different functions of the device for displaying X-ray images; and an image alternator (54) being operatively associated with said first screen (28) and said second screen (30) to automatically change the display of moving images of the object taken in one plane (P1) on the first screen (28) to display of moving images of the object taken in the other plane (P2) on the second screen (30) and vice versa, such that it becomes possible to see moving X-ray images of the object taken in the two different planes (P1 and P2) close behind each other.

2. The device according to claim 1, wherein the image alternator (54) is configured to carry through, during an image changing or succession procedure, a desired number of automatic image changes from having displayed moving X-ray images on one of the screens (28 or 30) to display moving X-ray images on another of said screens (30 or 28) and vice versa.

3. Device according to claim 1 including a control device (5), which can be activated and deactivated manually, to control the duration of the image changing or succession procedure.

4. Device according to claim 1, wherein the image alternator (54) is provided to carry through automatic changes or successions of images within an interval of from two image changes per second to one image change per two seconds.

5. Device according to claim 1, wherein the image alternator (54) is configured to freeze moving X-ray images to immovable X-ray images on one of the screens (28, 30) when it automatically changes to display moving X-ray images on the other screen (28, 30) such that immovable X-ray images are displayed on one of the screens (28, 30) while moving X-ray images are displayed on the other of said screens (28, 30).

6. Device according to claim 1, wherein the screens (28, 30) on which the X-ray images are displayed, are located above a control screen (33) and that said screens (28, 30) are pivotable about a vertical geometric axis (VA).

7. Device according to claim 1, wherein the first as well as the second screens (28 and 30) are located on the control centre (4).

8. Device according to claim 1, wherein the at least one brake apparatus (37 and/or 39) is provided on one of the wheel units (8 or 9).

9. Device according to claim 1, wherein one of the brake apparatus (37 or 35 or 36)) is provided on the one of the two wheel units (8, 9), another one of the brake apparatus (37 or 35 or 36) is provided on the other one of the two wheel units (8, 9).

10. Device according to claim 1, wherein the arm (18) is movably mounted on the arm brackets (13, 14) such that it can be pivoted or rotated about a geometric point (GC) for the arm, and said arm (18) carrying the said transmitters (21, 23) and said receivers (22, 24) of the X-ray devices (19, 20).

11. Device according to claim 1, including remote radio controllable operating devices (25a and 26a respectively) operatively associated with the receivers (22 and 24 respectively), wherein the receivers (22 and 24 respectively) are movable while they are operated by the remote radio controllable operating devices (25a and 26a respectively).

* * * * *